(12) United States Patent
Hammoud et al.

(10) Patent No.: US 7,742,621 B2
(45) Date of Patent: Jun. 22, 2010

(54) DYNAMIC EYE TRACKING SYSTEM

(75) Inventors: Riad I. Hammoud, Kokomo, IN (US);
Phillip V Malawey, Kokomo, IN (US)

(73) Assignee: Delphi Technologies, Inc., Troy, MI (US)

( * ) Notice: Subject to any disclaimer, the term of this patent is extended or adjusted under 35 U.S.C. 154(b) by 815 days.

(21) Appl. No.: 11/452,116

(22) Filed: Jun. 13, 2006

(65) Prior Publication Data
US 2007/0286457 A1 Dec. 13, 2007

(51) Int. Cl.
*G06K 9/00* (2006.01)
(52) U.S. Cl. .................. 382/103; 382/117; 382/118
(58) Field of Classification Search ............ 382/103, 382/117, 118
See application file for complete search history.

(56) References Cited

U.S. PATENT DOCUMENTS

| 5,859,921 | A | 1/1999 | Suzuki |
| 5,878,156 | A | 3/1999 | Okumura |
| 6,652,458 | B2 | 11/2003 | Blazey et al. |
| 6,859,144 | B2 | 2/2005 | Newman et al. |
| 6,873,714 | B2 | 3/2005 | Witt et al. |
| 6,926,429 | B2 | 8/2005 | Barlow et al. |
| 2003/0146901 | A1* | 8/2003 | Ryan .................... 345/158 |
| 2004/0179716 | A1* | 9/2004 | Tafuku et al. ........... 382/103 |
| 2005/0100191 | A1 | 5/2005 | Harbach et al. |
| 2005/0213792 | A1 | 9/2005 | Hammoud |
| 2005/0232461 | A1 | 10/2005 | Hammoud |
| 2006/0215017 | A1* | 9/2006 | Cohen et al. ......... 348/14.16 |

FOREIGN PATENT DOCUMENTS

| JP | 10236181 | 9/1998 |
| JP | 2001/001786 | 1/2001 |

OTHER PUBLICATIONS

EP Search Report dated Nov. 5, 2007.

\* cited by examiner

*Primary Examiner*—Samir A Ahmed
*Assistant Examiner*—Fred Hu
(74) *Attorney, Agent, or Firm*—Jimmy L. Funke

(57) ABSTRACT

A dynamic eye tracking system to track movement of an eye including the steps of detecting if a neighbor exists about the eye over a predetermined amount of time and forming a boundary for the neighbor. Eye candidates are tracked and a determination is made if the eye candidates are beyond the boundary defined by the detected neighbor.

7 Claims, 9 Drawing Sheets

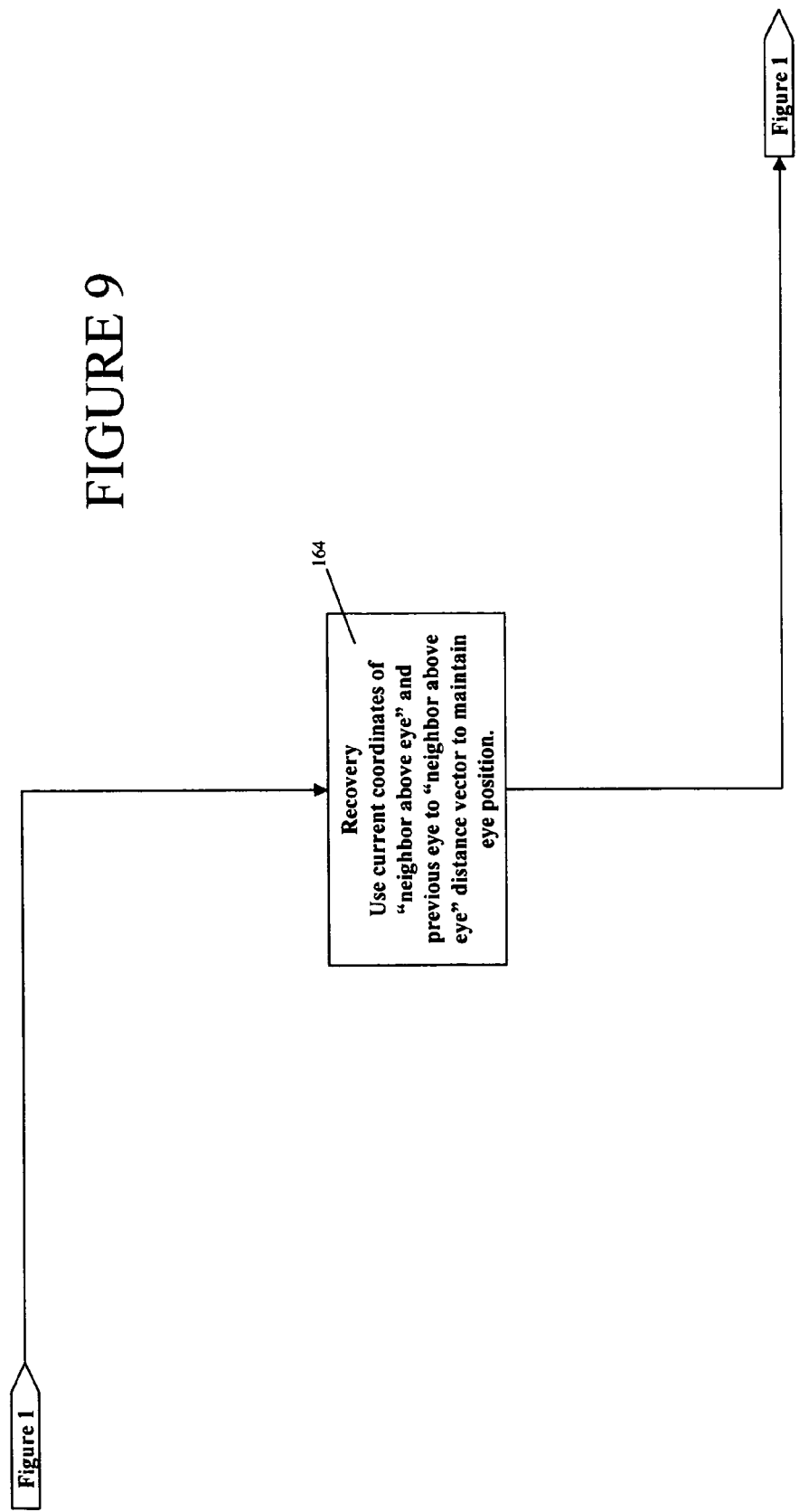

DYNAMIC EYE TRACKING SYSTEM

TECHNICAL FIELD

The field of this invention relates to an improved method of eye tracking for a driver state monitoring system and the like.

BACKGROUND OF THE DISCLOSURE

Driver state monitors are intended to track the movement of the eye and determine if the driver is becoming distracted or drowsy. In the motor vehicle environment for example, a camera can be used to generate an image of the driver's face and portions of the image can be analyzed to assess a driver's gaze or drowsiness. If such a condition exists, the system can detect the condition and provide an appropriate signal that can set off an alarm to either awaken the driver or alert the driver.

Eye position tracking in two dimensional grey scale image sequences must be at small time intervals to be useful for monitoring purposes. The eye position tracking must also be precise in tracking the eye center in two dimensional images and avoid drift during position tracking due to light changes in outdoor conditions. Other obstacles may also cause the monitoring to be ineffective. Major head motion such as turning the head, closure of the eye lid such as blinking, blink frequency, existence of glasses and sunglasses may all be conditions that may cause a monitoring system to fail by mistracking the eye position.

One of the most challenging problems in computer vision remains the eye position tracking problem. Image processing, computer vision and pattern recognition tools like mathematical morphological operators, contour extraction, interest point detector, eigen analysis and Kalman filter have been utilized in target tracking in visible and infrared imagery. In eye position tracking, it is common to extract the iris area and track it in successive frames with contour-based methods like active contour. Methods like bottom-hat morphological operators are usually employed in extracting the dark facial features in a face image. When dark feature like iris-eye and eyebrow are merged together into one big dark area due to shadow then the bottom-up morphological operator is not helpful. Another way being introduced to work around this issue is inverse receptive hole extractor (IRHE). Tracking methods like Kalman filter and correlation based techniques have some limitations when tracking the eye position in closed and open states as well for any facial feature complexity (dark-features vs. light-features, with and without glasses, with and without eyebrow, eye makeup, etc.). They tend to lose tracking of the eye or track the eye neighbors when the eye goes from open to closed. In particular, computer vision analysis systems such as Receptive Extraction or Inverse Receptive Hole Extraction (IRHE) techniques along with IRIS Extraction programs and Appearance-based Approach techniques have greatly improved tracking. These IRHE advances are disclosed in U.S. Ser. No. 11/300,621 filed on Dec. 14, 2005 by Riad Hammoud and entitled "Method of Locating a Human Eye in a Video Image" and are incorporated herein by reference.

Other methods as disclosed in U.S. Ser. No. 11/150,684 filed on Jun. 10, 2005 by Riad Hammound and Andrew Wilhelm and entitled "System and Method of Detecting an Eye" and U.S. Ser. No. 10/828,005 filed on Apr. 10, 2004 by Riad Hammoud and entitled "Object Tracking and Eye State Identification Method" are also incorporated herein by reference. However, even with other systems such as Single Template Correlation and Four Moving Parts Systems, these methods performed poorly in the tracking subjects with cluttered eye region of first order (for example, eyebrow or eyeglasses being present). Tracking subjects with a cluttered eye region, that is, an eye region where eyeglasses or eyebrows are in close proximity may result in tracking the eyebrow or the eyeglasses rather than the eye which can result in errors in measuring driver state such as driver fatigue or driver distraction.

What is needed is a dynamic improved eye position tracking system which takes into account located and tracked neighbors such as eyebrows or eyeglass frames to determine a constrained search window in which the eye must be located which improves the eye position tracking.

SUMMARY OF THE DISCLOSURE

This invention provides a eye tracking method for use in driver state monitors and the like which provides improved accurate eye tracking even when the eye being tracked is located in a cluttered eye region. The seminal idea of this novel method is to recognize that the subject appears with a neighbor for example, an eyebrow during tracking, and then to track both eye and the neighbor and to eliminate an eye candidate if it is beyond a dynamic moving boundary defined by the neighbor.

In accordance with one aspect of the invention, a dynamic eye tracking system to track movement of an eye includes detecting if a neighbor exists around the eye using initial coordinates of the eye for over a predetermined amount of time for example till the next video frame within a predefined area. A boundary is then formed for the neighbor within the predefined area. Potential eye candidates are tracked and the eye candidates are eliminated if they are beyond the boundary defined by the detected neighbors within said predefined area.

In one embodiment, the system determines if there is a persistent neighbor above the eye and determining if the eye image is merged with an image of the neighbor around the eye. If so, this system offsets a previously known boundary position by the change in the eye position.

If there is no persistent neighbor above the eye or if there is a persistent neighbor above the eye but no neighbors are merged with the eye, then, the dynamic eye tracking system preferably compares a local inverse receptive hole extraction for candidates not past the boundary and a local iris candidate not past the boundary to provide an eye candidate.

If the local inverse receptive hole extraction and the local iris extraction provides no acceptable eye candidate, the dynamic eye tracking system preferably uses a single template correlation by comparing with pre-loaded acceptable images of eyes to determine if there is an eye and then determine if the eye candidate is beyond the boundary determined by the neighbors. It is also desired that the dynamic eye tracking system compares previously saved templates from above, below, to the left and to the right of the eye and find a predetermined minimum correlation and execute an appearance check at the intersection of vertical lines between above and below templates and a horizontal line extending between left and right eye templates.

In accordance with another aspect of the invention, a dynamic eye tracking system executes in sequence any one of a series of eye candidate subroutines to determine if an acceptable eye candidate exists and for each subroutine then determines if the eye candidate is beyond or within a boundary defined by the neighbors within a predefined area.

BRIEF DESCRIPTION OF THE DRAWINGS

Reference now is made to the accompanying drawings in which:

FIG. 9 is a subsidiary flow chart detailing a neighbor to eye recovery subroutine section 164 shown in the master flow chart of FIG. 1.

DETAILED DESCRIPTION OF THE PREFERRED EMBODIMENT

Figure 1:
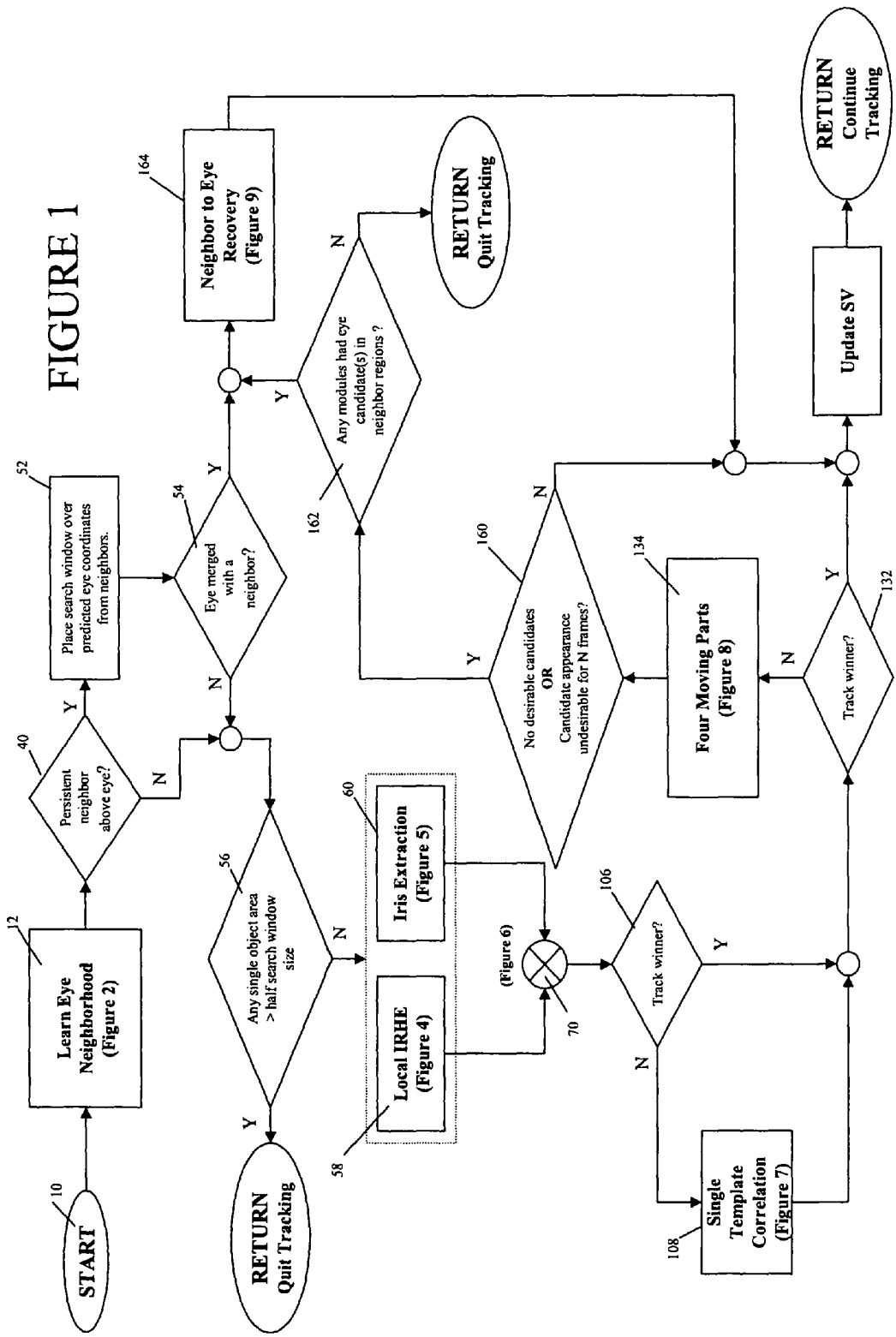
FIG. 1 is a master flow chart illustrating one embodiment of an eye tracking system according to the invention.
Figure 2:
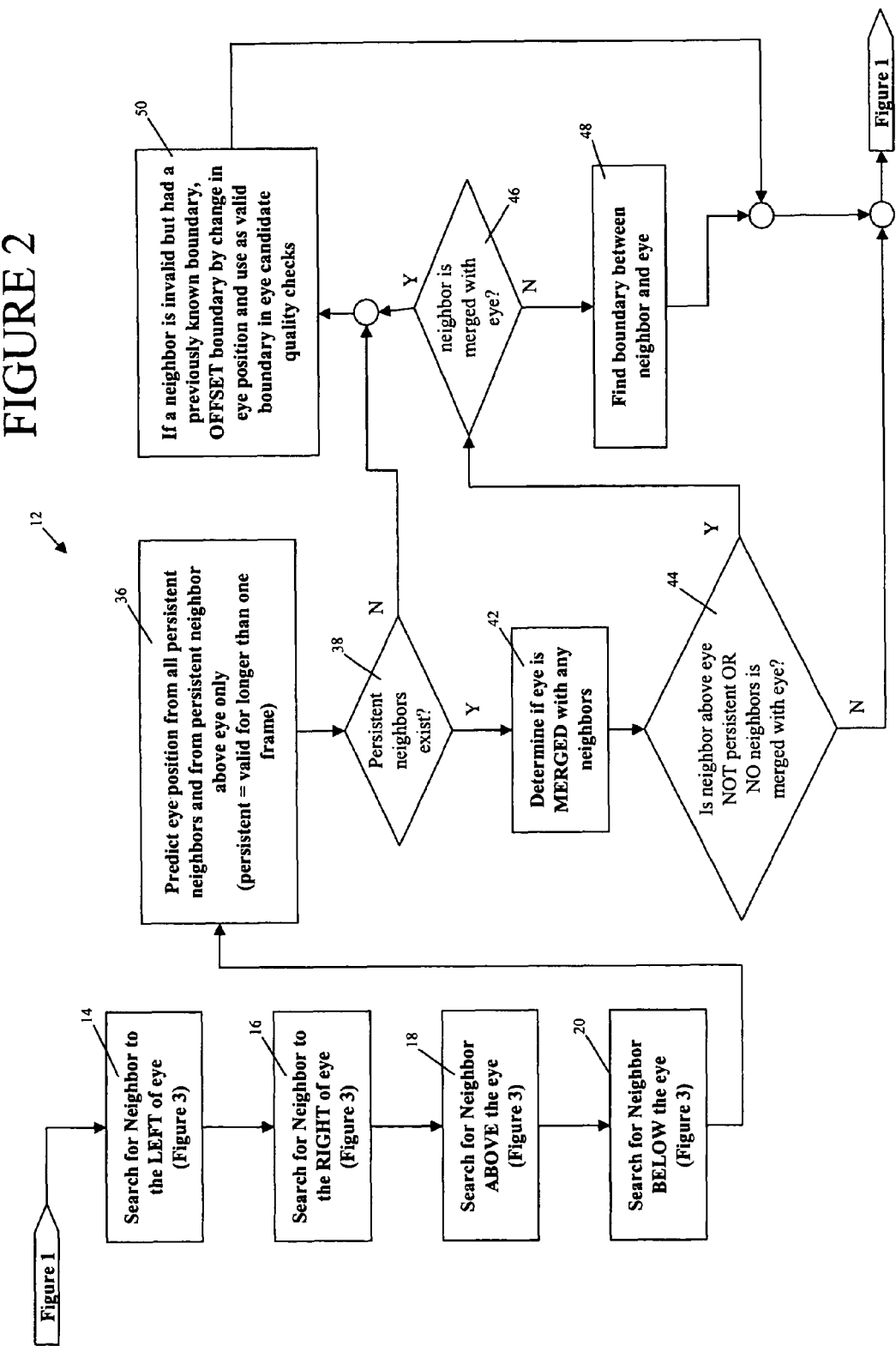
FIG. 2 is a subsidiary flow chart detailing a learn eye neighborhood subroutine section 12 shown in the master flow chart of FIG. 1.

Referring now to FIG. 1, a dynamic routine tracking system is shown where at the start 10, initial eye coordinates, found by an eye detection system, are passed to an eye tracking algorithm. Known speeds for eye tracking devices are about 30 frames per second to find eye coordinates and to track eye location. After the initial eye coordinates are determined, the eye neighborhood is then determined at 12 for each new frame taken. For example, the system determines if an eyebrow exists, tracks it, and determines if it is merged with the eye. Another example is to determine if an eyeglass rim exists. Subroutine 12 is shown in more detail in FIG. 2.

Figure 3:
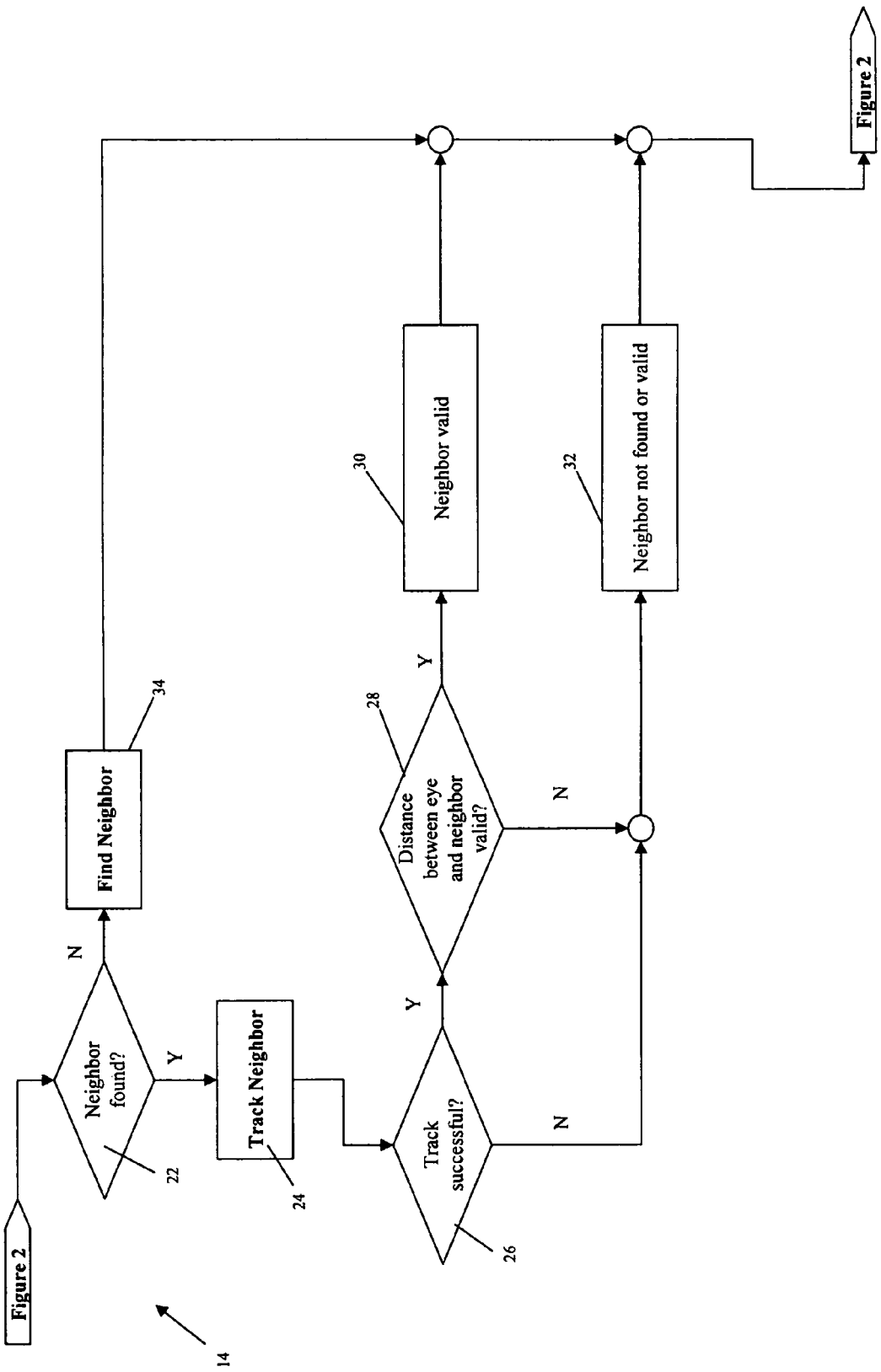
FIG. 3 is a subsidiary flow chart detailing a searching for neighbors subroutine section 14 of the subsidiary flow chart shown in FIG. 2.

The neighbor to the left, right, above and below the eye is searched for and found by subroutines 14, 16, 18, and 20. Each of the subroutines 14, 16, 18 and 20 is identical in form and is illustrated in FIG. 3. The question is asked if a neighbor has not been previously found such as an eyebrow or glass frame section at 22. If not, then a neighbor is searched for at 34 by finding a center Receptive Hole Extraction (RHE) component in a neighbor detection window. For example a window may be 32×80 pixels for the UP and DOWN window and 96×32 pixels for the left and right neighbor search windows. One then goes back to the subroutine shown in FIG. 2.

On the other hand, if the neighbor is found, then the neighbor is tracked at 24 by finding a center Receptive Hole Extraction (RHE) component in the neighbor tracking window. A neighbor tracking window may be 96×32 pixels for UP and DOWN neighbors and 48×32 pixels for LEFT and RIGHT neighbors. An inquiry is made to determine if the tracking was valid at 26. If so, the distance between the eye and the neighbor is measured and questioned to be within valid parameters. For example, Xmin Left/Right=20 pixels; Xmax Left/right=80 pixel; Ymin Left/Right=15; Ymax Left/Right=20 pixels; Ymin up/Down=15 pixels; Ymax Up/Down=60 pixels; and Xmax up/down=40 pixels. If the parameters are valid, the neighbor is valid at 30 and the subroutine returns to FIG. 2. If the parameters are invalid, the neighbor is denoted as not found or invalid and the subroutine is returned to FIG. 2.

After the subroutines 14, 16, 18 and 20 are each performed once as above described, subroutine 12 continues by predicting the eye position from all the persistent neighbors at 36. For purposes of this invention, the term "persistent" means that the neighbor occurs or is detected in more than one successive frame. The question is asked after predicting the eye position if any persistent neighbors exist at 38. If a particular persistent neighbor does not exist and that neighbor has a valid previously known boundary, the offset boundary is changed by the change in eye position and is used as a valid boundary in eye candidate quality checks at 50. The subroutine ends and goes back to main routine in FIG. 1 at 40.

On the other hand, if a persistent neighbor exists, it is then determined if any valid neighbors are merged with the detected eye at 42. After this determination is made, if the neighbor above the eye, for example, an eyebrow or eyeglass frame is persistent and a neighbor is merged with the eye as determined at 44, one then goes back to main routine at 40. In other words, special importance is given to neighbors above the eye if they are persistent because they are usually associated with more stable objects like eyebrows or long, horizontal eyeglass frames.

If the neighbor above the eye is not persistent or there are no neighbors merged with the eye, the subroutine asks if a neighbor is merged with the eye at 46. If not, the boundary between the neighbor and eye is found at 48 and the subroutine ends and goes back to the main routine shown in FIG. 1 at 40.

If the neighbor is merged with the eye and the neighbor has a valid previously known boundary, the offset boundary is changed by the change in eye position and is used as a valid boundary in eye candidate quality checks at 50. The subroutine ends and goes back to the main routine shown in FIG. 1 at 40.

The main routine asks at 40 if the persistent neighbor above the eye was found from subroutine 12. If the persistent neighbor above the eye exists a search window over the predicted eye coordinates determined by the surrounding neighbors is then used at 52 to limit the search for the eye. This helps maintain tracking is case of motion. The eye is tracked and a determination is made if any neighbor is merged with eye at 54.

If no neighbor is merged with the eye at 54 or a persistent neighbor above the eye does not exist at 40; then a tracking search window is processed at the last known eye position or the predicted position from neighbors. If the area of any single object in the search window is greater than half the search window size at 56 then the tracking program is exited. If not, then two programs are run in parallel, namely a known local Inverse Receptive Hole Extraction (IRHE) program 58 and an Iris Extraction program 60.

Figure 4:
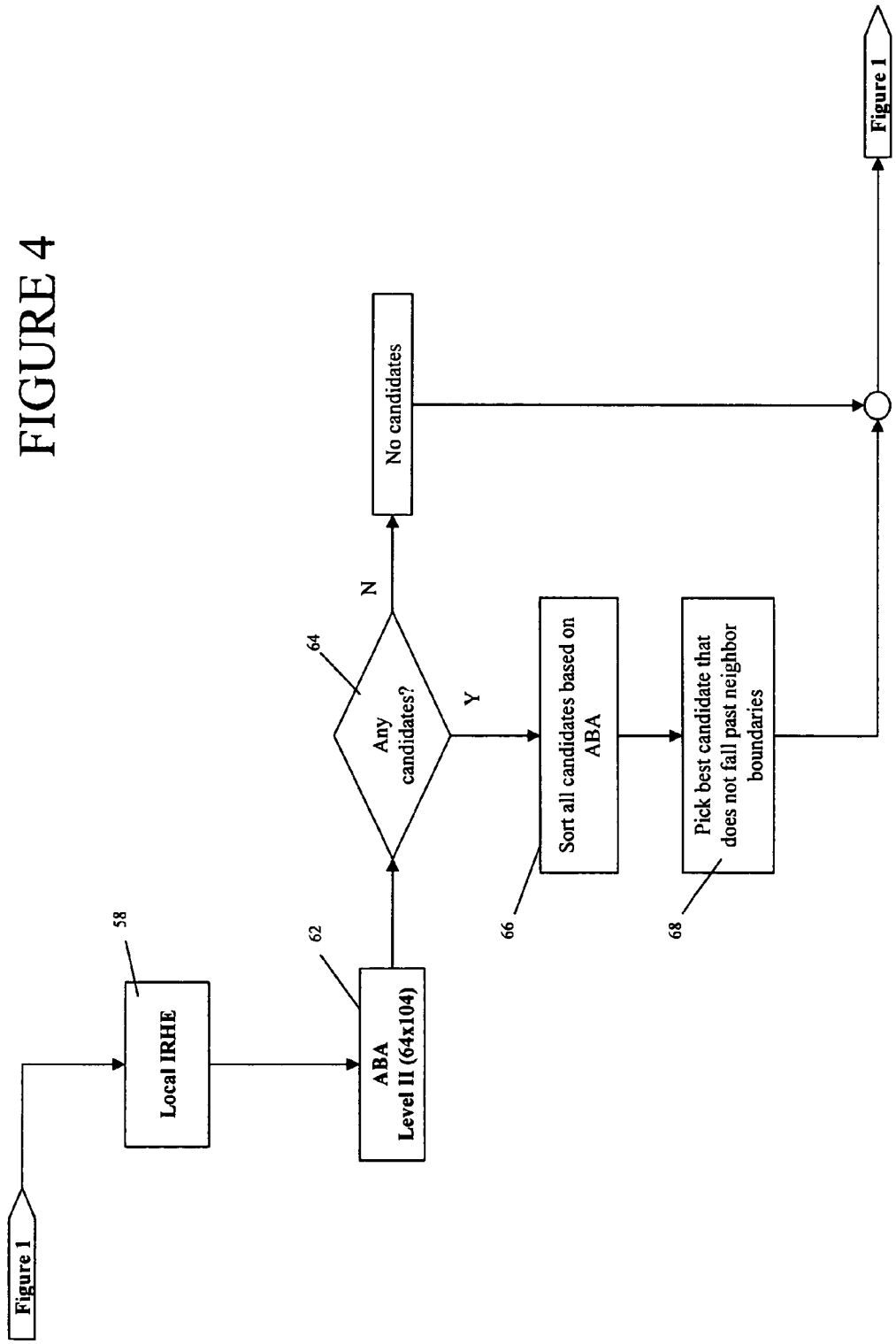
FIG. 4 is a subsidiary flow chart detailing a local inverse receptive hole extraction subroutine section 58 shown in the master flow chart of FIG. 1.

The Local IRHE program 58 is shown in more detail in FIG. 4. It uses a known Appearance-based Approach at 62 which the candidates that look like an eye from its database. The Appearance-based Approach uses a wider level which uses a larger region about the eye that includes neighbors. If there are any remaining eye candidates at 64, the program sorts them out using the appearance-based approach and saves all potential eye candidates in order of best appearance at 66. A second sort is done to determine which is the best candidate that does not fall past the neighbor boundaries at 68. The candidate or lack of candidate signal is then brought back to a comparator 70 at the main routine shown in FIG. 1.

Figure 5:
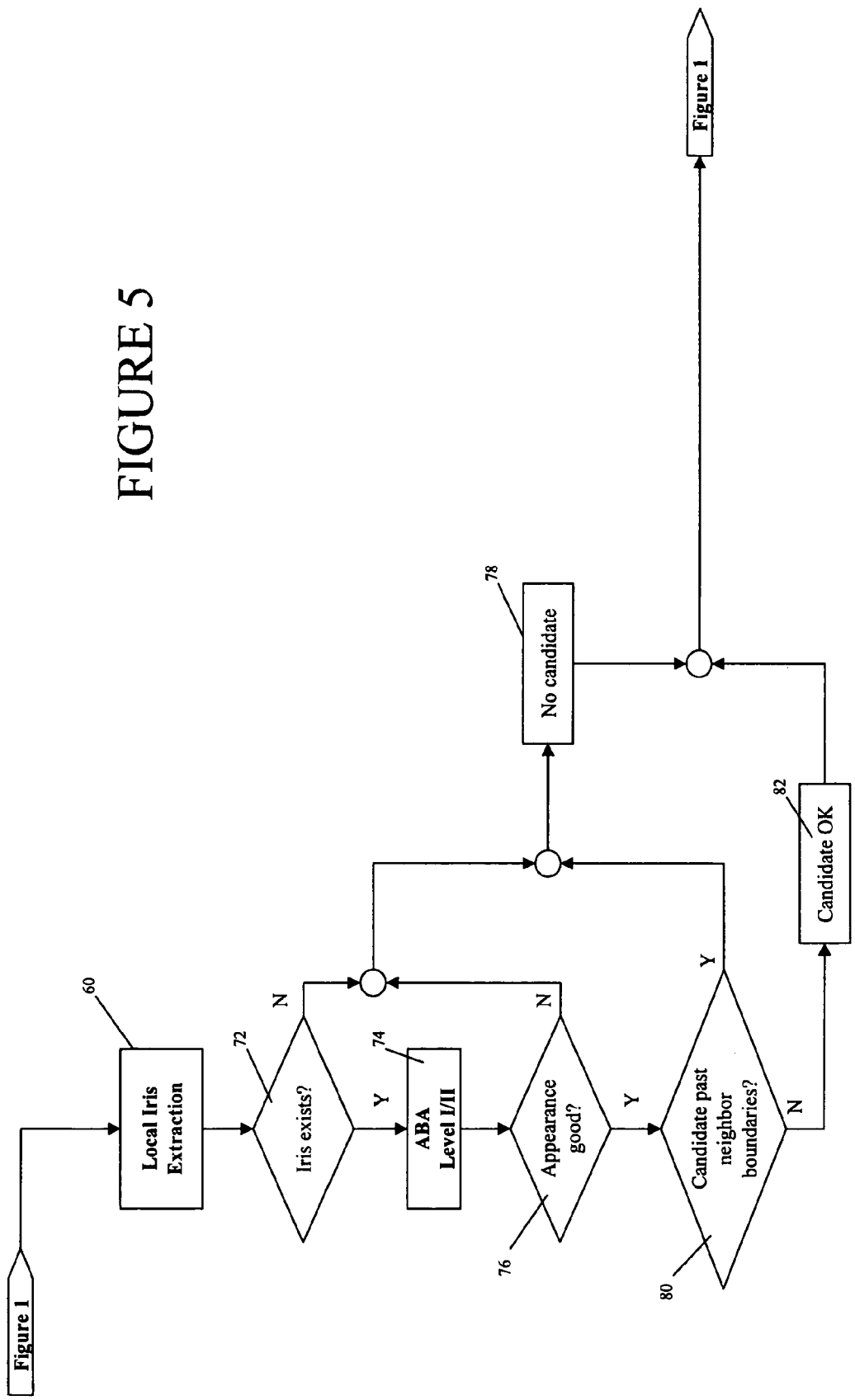
FIG. 5 is a subsidiary flow chart detailing an iris extraction subroutine section 60 shown in the master flow chart of FIG. 1.

The Iris Extraction Program 60 is shown in more detail in FIG. 5. The program 60 finds an RHE component closest to the center of the tracking search window with a predetermined minimum size for example 15 pixels. If the Iris candidate exists at 72 than it is verified with of a level I and/or II appearance checks. If no iris exists or the appearance-based approach program 74 determines that the candidates appearance is undesirable at 76 by it classification rules, then no candidate signal is formed at 78 and the program return to the main routine at 70.

If the appearance is determined to be good at 76, the candidate location is then determined at 80 and if is located beyond the boundary of the neighbor than it is rejected as a candidate. If the candidate is not outside the boundary, then it is determined to be an acceptable candidate at 82 and the program returns to the main program at 70.

Figure 6:
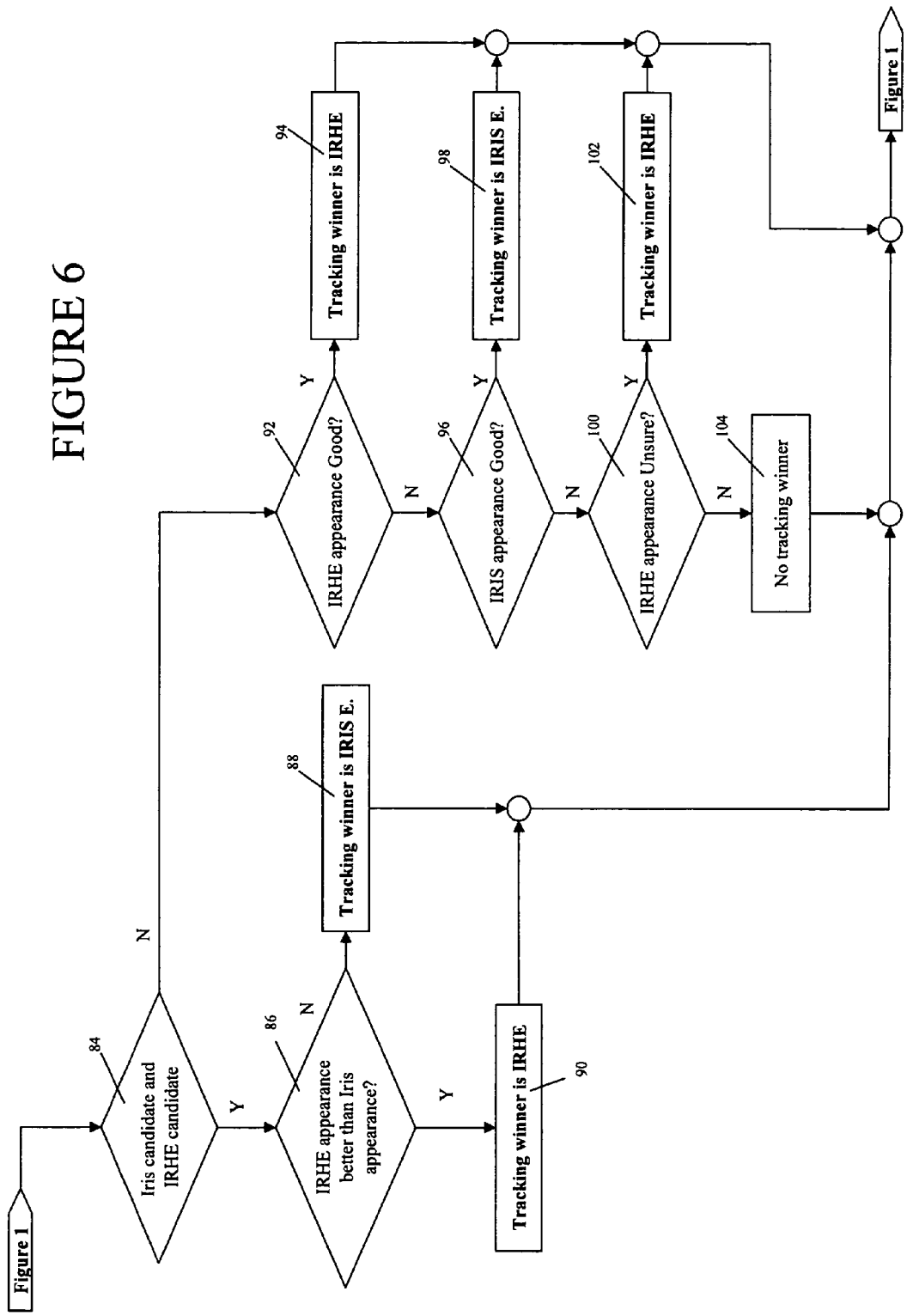
FIG. 6 is a subsidiary flow chart detailing a comparison subroutine section 70 shown in the master flow chart of FIG. 1.

Referring now to FIG. 6, the comparison between the two subprograms 58 and 60 is then made at 70 to determine which program candidate should be used. If both IRHE and IRIS candidates exist at 84, then the one with the best appearance is selected at either 88 or 90 and the subroutine returns to the main program at 106.

If only the IRHE candidate exists with desirable appearance at 92, then the comparator returns this candidate as winner at 94. Otherwise, if only the IRIS candidate appearance is good at 96 with desirable appearance, then return this candidate as winner at 98.

Otherwise if only the IRHE candidate exists with an unsure appearance at 100, this candidate is selected at 102. Otherwise there is no tracking winner selected at 104 and the subroutine returns to the main program at 106.

Figure 7:
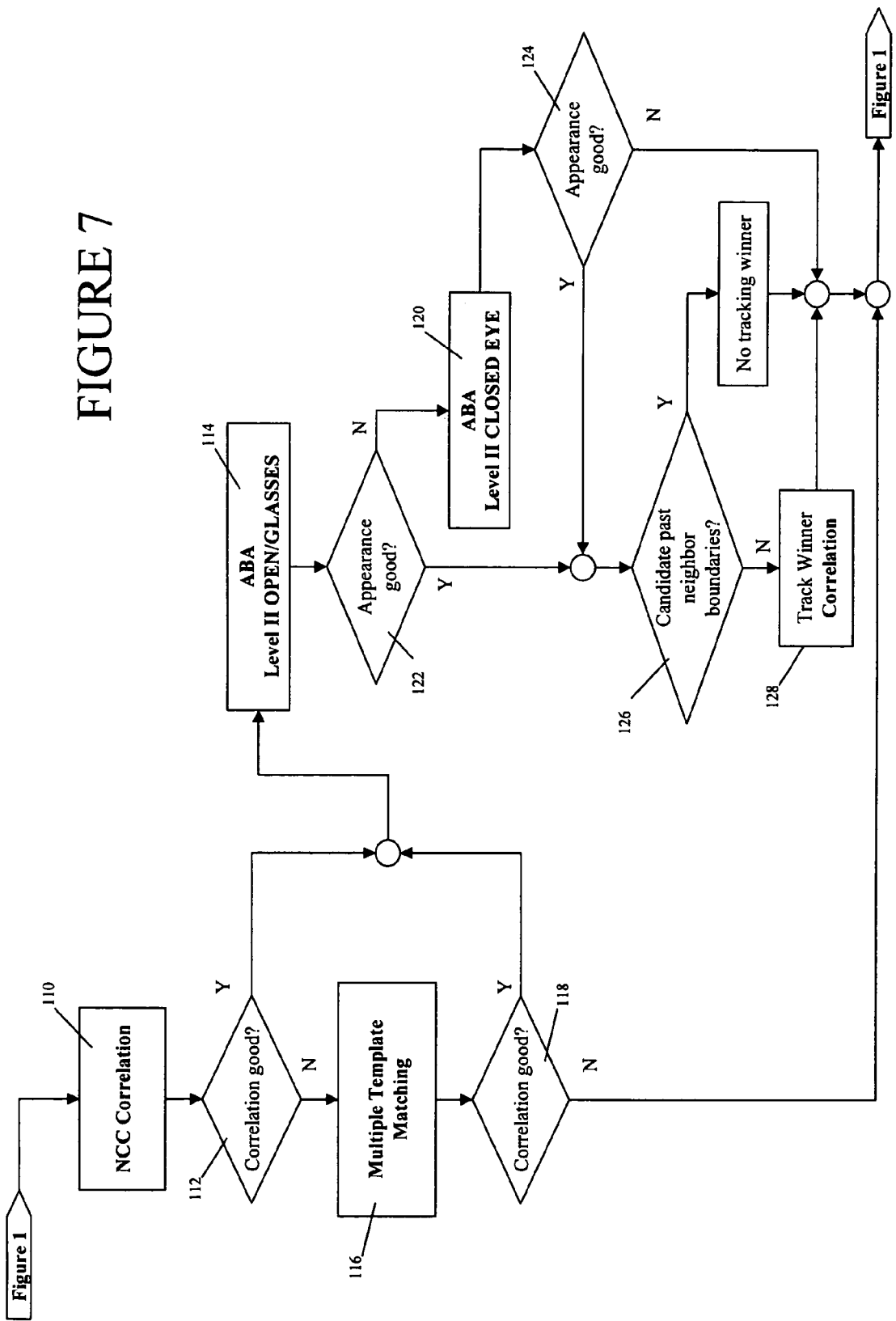
FIG. 7 is a subsidiary flow chart detailing a single template correlation subroutine section 108 shown in the master flow chart of FIG. 1.

If there is no track winner as indicated at 106, a Single Template Correlation 108 as shown in detail in FIG. 7 is implemented. The Single Template correlation first uses a normalized cross correlation (NCC) function at 110 to match eye template from the previous frame to current tracking search window. If the correlation is above an acceptable threshold as indicated at 112, then the candidate is verified with a known Level I and/or Level II Appearance-based Approach.

Otherwise a known multiple template matching routine 116 returns a good match, i.e. match four templates around last eye point to same points in current frame. If three or four templates correlate above a certain threshold, e.g. 65%, the previous eye position is valid at 118 and the subroutine return to the main program at 132. The previous eye position candidate is verified with Level II Open Eye and/or Closed Eye appearance-based approach at 114 and 120. If the candidate appearance is desirable at 122 or 124, then the candidate location is checked at 126. If it is not outside the boundary then it is determine to be an acceptable candidate at 128 and the program returns to the main program at 132. On the other hand, if the candidate is located beyond the boundary of the neighbor than it is rejected as a candidate and no winning candidate is determined and the subroutine returns to the main program 132 in FIG. 1.

Figure 8:
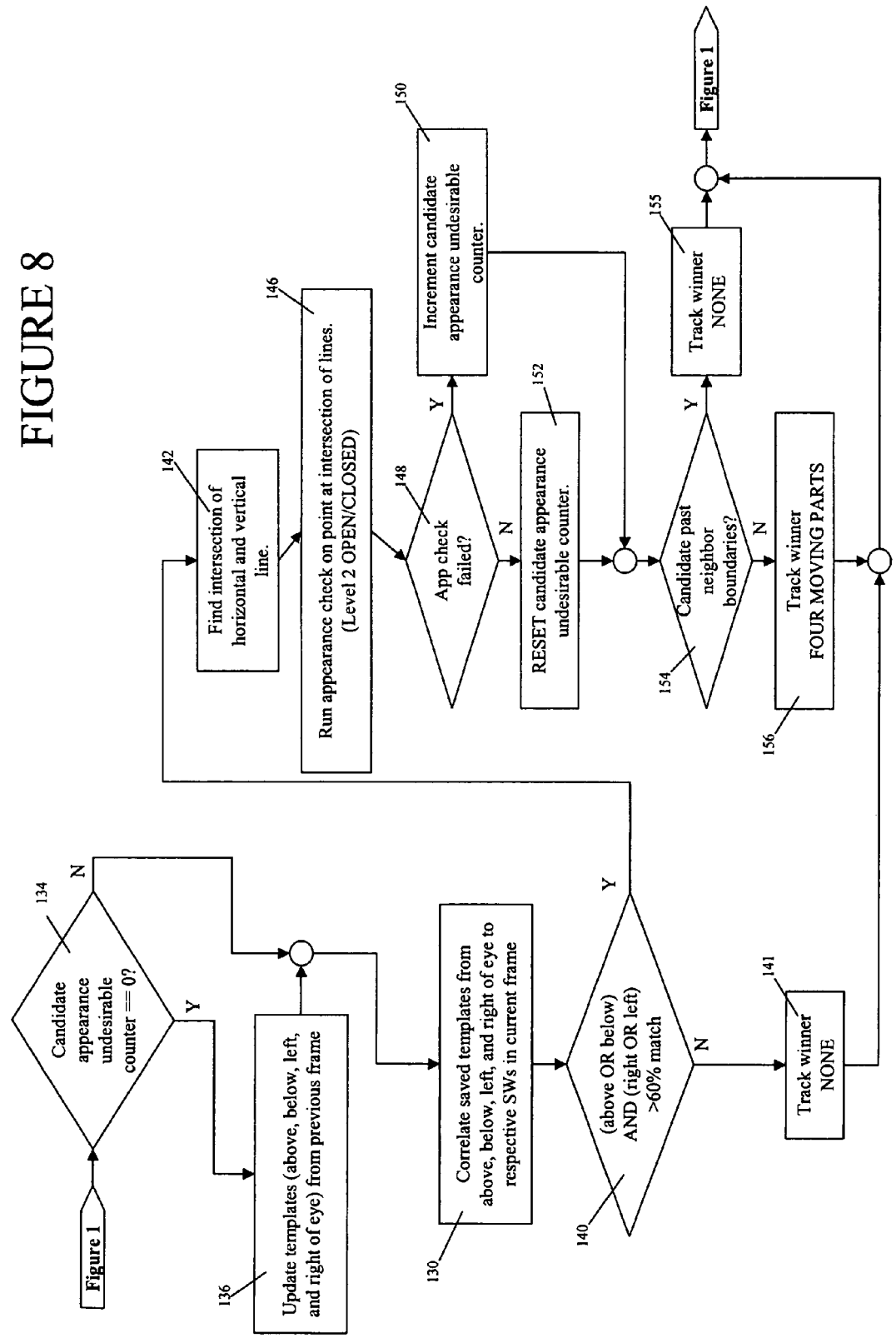
FIG. 8 is a subsidiary flow chart detailing a four moving parts subroutine section 134 shown in the master flow chart of FIG. 1.

If there is no track winner indicated at 132 than a Four Moving Parts subroutine 134 is executed. As shown in FIG. 8, the Four Moving Parts subroutine 134 first sees if 'candidate appearance undesirable' counter equal zero, then all templates around eye from previous frame are extracted and updated at 136. The updated templates are matched to corresponding search windows in current frame at 138. If at least one template from the vertical plane and one from the horizontal plane exceed the correlation threshold at 140 for example greater than 60% above and/or below eye AND left and/or right of eye, then the intersection of the horizontal and vertical lines is found at 142. The vertical line is the line drawn between the above and below the eye templates. The horizontal line is the line drawn between the left and right eye templates. On the other hand, if the correlation is less than 60% at 140, no track winner is indicated at the main program at 160.

After the intersection of the horizontal and vertical lines is found, a known Level II OPEN and CLOSED appearance check is conducted at 146. If it fails at 148, then candidate appearance undesirable counter 150 is incremented one count. The counter 150 is used to exit tracking if appearance fails for a certain number, N, of frames. If the appearance check did not fail, the counter is reset at 152.

The candidate location is then checked at 154. If the candidate is located beyond the boundary of the neighbor than it is rejected as a candidate. If it is not outside the boundary then it is determine to be an acceptable candidate at 156 and the subroutine returns to the main program at 160. Otherwise, if the candidate is past the boundaries of the neighbor, no winning candidate is determined at 155 and the subroutine returns to the main program at 160.

If no desirable eye candidate is found or a candidate's appearance from the Four Moving Parts subroutine is undesirable for a certain number of consecutive frames, for example 60 frames, it is then determined if any modules had eye candidate(s) in neighboring regions at 162. If not, the tracking program is exited. If so, then a Neighbor to Eye Recovery subroutine is initiated at 164. The Neighbor to Eye Recovery is also initiated if the eye is determined to be merged with a neighbor at 54.

The Neighbor to Eye Recovery subroutine is shown in more detail in FIG. 9. The current 'neighbor above eye' position and the previous eye to 'neighbor above eye' distance vector are used to find a new eye position. The State Vector is updated at 166 if there is a tracking candidate winner at 106 or at 132 or after the Neighbor to Eye Recovery 164 is performed. After the State Vector 166 is updated, the tracking program is exited and restarted at 10.

In this fashion, the tracking program becomes more robust by forming boundaries determined by detected persistent neighbors and using these boundaries to eliminate otherwise false positive tracking of the eye by determining that the candidate is beyond the boundary determined by the neighbor. Vast areas of detection may be eliminated and the tracking window can be more clearly concentrated near where the eye actually is.

Variations and modifications are possible without departing from the scope and spirit of the present invention as defined by the appended claims.

We claim:

1. A dynamic eye tracking method to track movement of an eye in video images from a camera, said method comprising:
   providing a camera;
   using a computerized eye state monitor having a computer readable medium;
   detecting if a neighbor exists about the eye using initial coordinates of the eye for over a predetermined amount of time within a predefined area;
   forming a boundary for said neighbor within said predefined area;
   tracking potential eye candidates; and
   determining if said eye candidates are beyond the boundary and eliminating the eye candidates outside the boundary defined by the detected neighbors within said predefined area.

2. A dynamic eye tracking method as defined in claim 1 further comprising:

determining if there is a persistent neighbor above said eye in successive video images; and determining if the eye image is merged with an image of said neighbor around said eye, and if so offsetting a previously known boundary of the neighbor by the change in the eye position to update said boundary for said merged neighbor image.

3. A dynamic eye tracking method as defined in claim 2 further comprising:

comparing a local inverse receptive hole extraction for candidates not past said boundary and a local iris candidate not past said boundary to provide an eye candidate if there is no persistent neighbor above said eye or said eye is not merged with said neighbor above said eye.

4. A dynamic eye tracking method as defined in claim 3 further comprising:

using a single template correlation by comparing with preloaded acceptable images of eyes to determine if there is an eye candidate if said local inverse receptive hole extraction and said local iris extraction provides no acceptable eye candidate, and to determine if said eye provided is beyond the boundary determined by said neighbor.

5. A dynamic eye tracking method as defined in claim 4 further comprising:

comparing previously saved templates from above, below, to the left, and to the right of the eye and find a predetermined minimum correlation and execute an appearance check at the intersection of a vertical line between above and below templates and a horizontal line between left and right eye templates.

6. A dynamic eye tracking method as defined in claim 1 further comprising:

executing in sequence any one of a series of eye candidate subroutines to determine if an acceptable eye candidate exists and for each subroutine then determine if said eye candidate is beyond or within a boundary defined by said neighbors within a predefined area.

7. A dynamic eye tracking method to track movement of an eye in video images from a camera, the method comprising:

providing a camera;

using a computerized eye state monitor having a computer readable medium;

executing in sequence any one of a series of eye candidate subroutines to determine if an acceptable eye candidate exists; and for each subroutine then determining if said eye candidate is beyond or within a boundary defined by said neighbors within a predefined area.

* * * * *